US005273523A

United States Patent [19]

Sozuki et al.

[11] Patent Number: 5,273,523

[45] Date of Patent: Dec. 28, 1993

[54] GASTRIC TUBE WITH FLUID INJECTION ADAPTOR

[75] Inventors: Nobuaki Sozuki; Yosuke Okada, both of Shizuoka, Japan

[73] Assignee: Sherwood Medical Company, St. Louis, Mo.

[21] Appl. No.: 909,932

[22] Filed: Jul. 7, 1992

[30] Foreign Application Priority Data

Jul. 12, 1991 [JP] Japan ............................ 3-054188[U]

[51] Int. Cl.[5] ............................................ A61M 27/00

[52] U.S. Cl. ........................................ 604/43; 604/28; 604/31; 604/45; 604/283

[58] Field of Search ............ 604/27, 30, 31, 35-37,43, 604/45, 54, 128, 129, 247, 256, 268, 283, 28

[56] References Cited

U.S. PATENT DOCUMENTS

| | | | |
|---|---|---|---|
| 3,087,492 | 4/1963 | Garth | 128/350 |
| 3,726,282 | 4/1973 | Patel | 128/349 BV |
| 4,573,965 | 3/1986 | Russo | 604/45 |
| 4,735,607 | 4/1988 | Keith, Jr. | 604/54 |
| 4,850,393 | 7/1989 | Lashomb | 604/45 |
| 4,881,542 | 11/1989 | Schmidt et al. | 604/43 |

FOREIGN PATENT DOCUMENTS 2127295 9/1982 United Kingdom .

*Primary Examiner*—John D. Yasko
*Assistant Examiner*—Anthony Gutowski
*Attorney, Agent, or Firm*—David A. Warmbold; Gene B. Kartchner; Montgomery W. Smith

[57] ABSTRACT

A double lumen gastric tube including a valve to prevent gastric reflux or leakage through the vent lumen thereof. The gastric tube also includes an adaptor which allows fluid injection through the tube without removing the valve. The valve allows the passage of air into the vent lumen when atmospheric pressure exceeds stomach pressure. When stomach pressure exceeds atmospheric pressure the valve prevents flow of fluid through the tube. The adaptor allows fluid to be injected into the vent lumen through the valve.

2 Claims, 3 Drawing Sheets

GASTRIC TUBE WITH FLUID INJECTION ADAPTOR

BACKGROUND OF THE INVENTION

1. Field of the Invention

This invention relates generally to tubes which are inserted into the body. More particularly, the present invention relates to medical tubing such as gastric tubes which include an antireflux valve which is adapted to allow the injection of fluids through the tube without removal of the valve.

2. Prior Art

Medical tubes such as are commonly used for insertion into the body of a patient to administer or collect fluid are in common use in hospitals. A particular device of this nature is a nasogastric tube which is inserted through the nasal passage of the patient into the patient's stomach or intestine to remove fluid from the patient or to administer medications or nutritives.

For example, nasogastric tubes of this type may be used post operatively to prevent pooling of liquids in the stomach during the patient's recovery. Often, gastric tubes of this type are formed with dual lumens, including a primary suction lumen and a secondary vent lumen which communicate with each other at the distal end or tip of the tube by means of a small orifice therebetween. The suction lumen also includes a plurality of side holes formed therethrough near the distal tip of the catheter for allowing suctioned fluids to pass into the catheter from the stomach.

As is shown in U.S. Pat. No. 4,735,607 to Keith, Jr., nasogastric tubes often include a branching tube (identified as element 23 in the Keith, Jr. reference) which communicates with the secondary vent lumen of the tube and includes a check valve therein which functions to inhibit the flow of reflux fluid through the vent lumen and out of the tube to contaminate the patient area.

When in use for removing fluids from the stomach, the upper or proximal end of the gastric tube is ordinarily connected through a collector vessel to a vacuum pump system. Stomach fluids are then drawn through the side holes in the distal end of the tube and into the collector vessel. Often however, the side holes become clogged with stomach debris, or more seriously, by the inadvertent drawing of soft stomach wall tissue thereinto.

To help prevent blockage of the tubing side holes, the vent lumen of the dual lumen tube permits atmospheric air to be drawn through the small orifice at the distal end thereof into the suction lumen. This prevents over suctioning which could otherwise damage the stomach wall tissue. As is evident, proper operation of the double lumen tube depends on the continuous availability of atmospheric air to the suction openings through the small orifice between the suction lumen and the vent lumen at the distal end of the tube.

Unfortunately, double lumen nasogastric tubes frequently do not operate as intended, and stomach pressure becomes greater than atmospheric pressure allowing gastric reflux, or leakage, to occur through the vent lumen. This over pressure can be caused by the patient coughing, by over filling the stomach with air, or by external pressure on the stomach. Leakage of fluids due to gastric reflux can cause significant problems such as wound contamination, infections, etc., and significant time in clean up of the patient area by the hospital staff.

One very effective solution to the problem of gastric reflux has been to place an antireflux valve, such as that shown in the above-cited prior art patent to Keith, Jr., into the gastric tube at the proximal end of the vent lumen. The antireflux valve allows entrance of atmospheric air into the vent lumen, while preventing the passage of reflux fluid therepast. However, it is often necessary to inject fluids directly into the patient's stomach through the venting lumen for the purposes cf irrigation, medication, nutrition, etc. In the past, such procedures have required the removal of the antireflux valve to allow attachment of a syringe or the like for injecting fluid through the vent lumen. This necessity is less than satisfactory in that it often allows contamination of the patient area and/or bacterial ingress to occur through the vent lumen.

OBJECTS AND SUMMARY OF THE INVENTION

It is therefore an object of the present invention to provide a medical tube which includes an antireflux valve which prevents back flow therethrough, while at the same time allows fluid injection into the tube without removal of the antireflux valve.

Another object of the invention is to provide a method of injecting fluids into a gastric tube without the necessity of removing the antireflux valve thereof.

Another object of the invention is to provide such a method and device which are inexpensive and easy to use, and adaptable to various common medical procedures associated with gastric intubation.

These and other objects and advantages of the present are realized in a presently preferred embodiment, shown by way of example and not necessarily by way of limitation, which includes a dual lumen nasogastric tube having a primary lumen used as the suction lumen, and a secondary lumen used as a vent lumen, with each lumen communicating at the distal end of the tube through a small orifice. The venting lumen further includes a branching tube which communicates therewith and which is attached at its opposite end to an antireflux valve. An adaptor is connected to the antireflux valve opposite the branching tube and is designed to allow the passage of atmospheric air therethrough into the venting lumen, or alternatively, to allow attachment of an injection device such as a syringe, for the injection of fluid through the antireflux valve and the branching tube into the vent lumen.

DETAILED DESCRIPTION OF THE PREFERRED EMBODIMENTS

Figure 1:
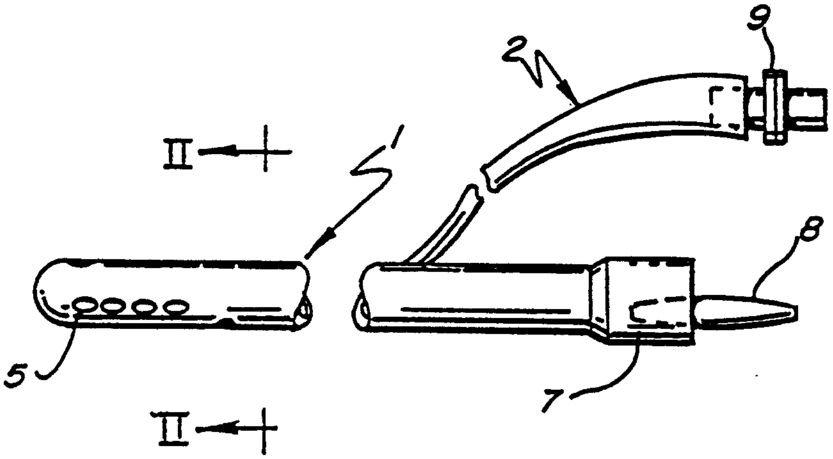
Fig. 1 (PRIOR ART)
FIG. 1 is a perspective view of a prior art nasogastric tube.
Figure 2:
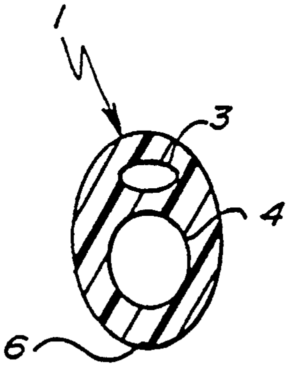
Fig. 2. (PRIOR ART)
FIG. 2 is a cross-sectional view taken along line II—II of the prior art device of FIG. 1.

As shown in FIGS. 1 and 2, a conventional dual lumen-type gastric tube is shown and identified as element 1. The tube 1 has formed thereon a branching tube 2 which is formed in fluid flow connection with the vent lumen 3 of the tube 1. The vent lumen 3 and suction lumen 4 of the tube 1 extend generally in parallel along the entire length of the tube 1, and are in fluid flow connection at the distal end thereof by a small orifice (not shown). Also at the distal end of the tube 1, a plurality of side holes 5 are formed to allow fluid flow from the patient's stomach into the suction lumen 4. A strip 16 of radiopaque material may also be included in the formation of the tube 1 if desired. At the proximal end 7 of the tube 1, a connector 8 may be inserted into the suction opening 4 to allow fluid flow connection of the suction lumen 4 with a suction source (not shown).

The proximal end of branching tube 2 includes an antireflux valve formed therein such as that shown and described in the above-mentioned U.S. Pat. No. 4,735,607 to Keith, Jr. The distal tip of the tube 1 is formed closed into a smooth semispherical shape.

Any required injection of fluid into the vent lumen 3 through the branching tube 2 requires the removal of the antireflux valve 9. Although the antireflux valve 9 of the prior art device is effective in preventing reflux of patient's fluids through the vent lumen 3, it is ineffective for allowing injection of fluids. With the prior art device, it is generally necessary to halt suctioning while the branching tube 2 is being manipulated and the antireflux valve 9 is being removed therefrom to allow attachment of a fluid injection device such as a syringe. This is inconvenient and can cause the inadvertent loss of the antireflux valve 9. Further, the procedure allows for possible contamination of the patient area and possible bacterial ingress into the tube 1 through the branching tube 2.

The present invention solves the problems inherent in the prior art device occasioned by the necessity of removing the antireflux valve 9 thereof prior to injection of fluids into the vent lumen. This is accomplished in the present invention by providing the gastric tube 10 with an antireflux valve 20 which prevents back flow through the vent lumen 13 thereof while at the same time allows fluid injection therethrough, thus obviating the necessity of its removal.

Figure 3:
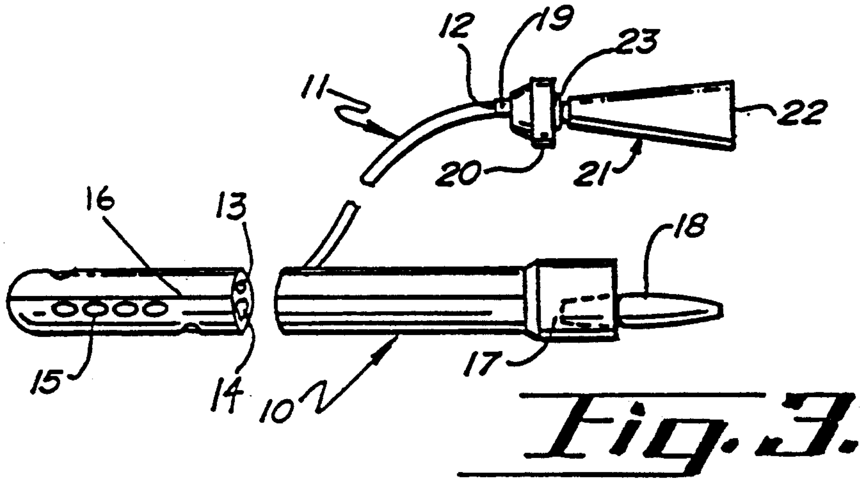
FIG. 3 is a perspective view of a nasogastric tube formed in accordance with the principles of the present invention.
Figure 4:
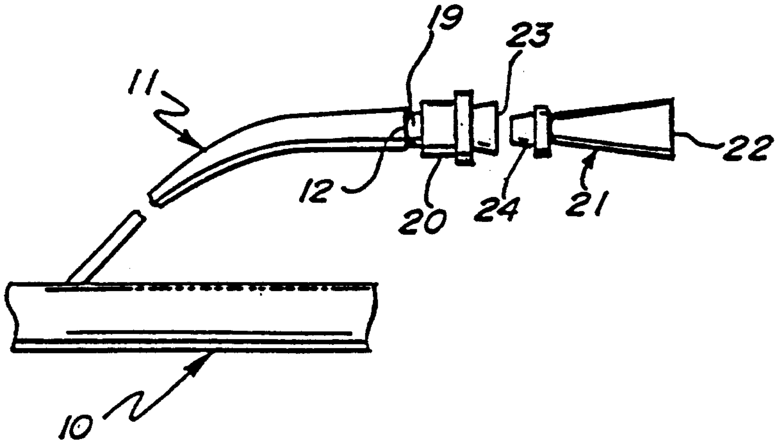
FIG. 4 is a perspective view of the most relevant portion of another preferred embodiment of a nasogastric tube formed in accordance with the principles of the present invention.
Figure 5:
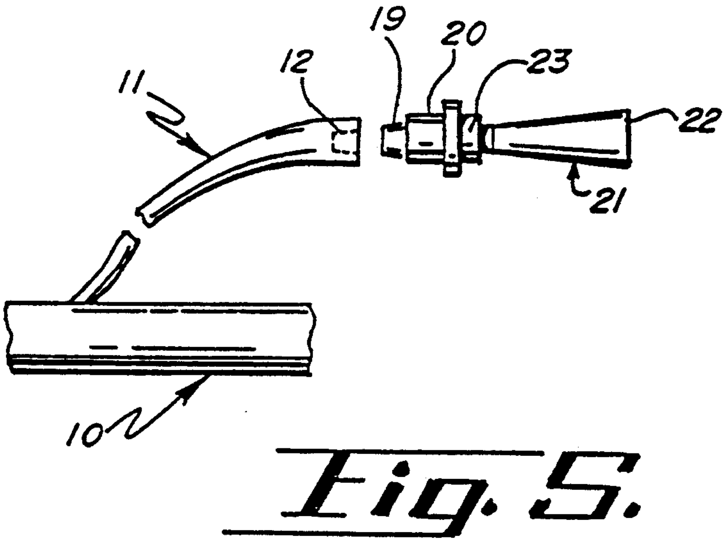
FIG. 5 is a perspective view of the relevant portion of a further preferred embodiment of a nasogastric tube formed in accordance with the principles of the present invention.

As shown in the exemplary FIGS. 3–5, for the purposes of illustration, a nasogastric tube made in accordance with the principles of the present invention, referred to generally by the reference numeral 10, is provided for nasogastric intubation of a patient with the prevention of fluid reflux through the venting tube thereof while at the same time allowing the injection of fluids therethrough.

More specifically, as shown in FIG. 3, the gastric tube 10 of the present invention is formed of a dual lumen catheter having a vent lumen 13 and a suction lumen 14 therein, the suction lumen 14 includes side holes 15 formed therein at its distal end, and the vent lumen 13 and suction lumen 14 are joined in fluid flow connection at their distal end by a small orifice (not shown). The proximal end 17 of the tube 10 is formed to allow a connector 18 to be inserted into the suction lumen 14 in order to allow attachment of the tube 10 to a suction source (not shown). The tube 10 further includes a branching tube Il which is formed at its distal end to be in fluid flow connection with the vent lumen 13, and at its proximal end to be in fluid flow connection with the antireflux valve 20.

In accordance with the principles of the present invention, a distal end 19 of the antireflux valve 20 is preferably bonded or permanently fitted at the proximal end 12 of the branching tube 11. A proximal end 23 of the antireflux valve 20 is then attached to an adaptor 21.

The adaptor 21 allows atmospheric air to pass therethrough into the antireflux valve 20, and from there through the branching tube 11 into the vent lumen 13 Due to the fluid flow connection between the adaptor 21 and the antireflux valve 20, fluid injection is possible without removal of the antireflux valve 20 from the branching tube 11. It is anticipated that the adaptor 21 be formed at its proximal end 22 with a luer tip or other type of common connector to facilitate attachment thereto of a fluid injection device such as a syringe or the like, for the injection of fluids.

As illustrated in FIG. 3, the antireflux valve 20 is attached at the proximal end 12 of the branching tube 11. The adaptor 21 on the proximal side of the antireflux valve 20 is provided with an open end 22 of luer size or catheter size. The proximal end 12 of the branching tube 11, and the distal end of the adaptor 21 are fixed to the antireflux valve 10, respectively at its distal end 19 and proximal end 23, by bonding or resilient compression, and are therefor formed to function as a single unit under ordinary circumstances. The actual valving mechanism enclosed within the antireflux valve 20 is not intended to be limited by the present invention, and may be of duck-bill, umbrella, mushroom, or like design.

FIG. 4 illustrates another embodiment of the present invention in which the antireflux valve 20 is attached to the proximal end 12 of the branching tube 11 by bonding or the like, and the proximal side 23 of the antireflux valve 20 is formed with a fitting such as a female luer fitting, and the distal end of the adaptor 21 is formed with a fitting 24 such a male luer fitting to allow connection between the adaptor 21 and the proximal side 23 of the antireflux valve 20.

FIG. 5 shows a further preferred embodiment of the present invention in which the proximal end 12 of the branching tube 11 is forced in a tapered fashion into a female luer fitting, and the distal end 19 of the antireflux valve 20 is formed into a male luer fitting for connection with the proximal end 12 of the tube 11. This embodiment may be useful in the event that it becomes necessary to unclog the suction lumen 14 by applying suction through the vent lumen 13. In such an instance, it would be a simple matter to remove the antireflux valve 20 from the branching tube 11 and insert a syringe or like device having a male luer fitting thereon into the female luer fitting formed in the proximal end 12 of the tube 11.

It will be apparent from the foregoing that, while particular embodiments of the invention have been illustrated and described, various modifications can be made thereto without departing from the spirit and scope of the present invention. Accordingly, it is not intended that the invention be limited, except as by the appended claims.

What is claimed is:

1. A gastric tube comprising:

a primary lumen including means for attaching a proximal end of said primary lumen to a suction source, said gastric tube forming at least one side hole therein which is in fluid communication with a distal end of said primary lumen, a secondary lumen, said secondary lumen being in fluid flow communication at a distal end thereof with said primary lumen and at a proximal end thereof with an antireflux valve means, and said antireflux valve means including adaptor means formed at a proximal end of said antireflux valve for allowing injection of a fluid therethrough into said secondary lumen, said adaptor means having an unobstructed passageway therethrough, the adaptor means having a male luer taper thereon and said antireflux valve means having a female luer taper thereon for connection to said male luer taper of said adaptor means.

2. A method of performing irrigation through a gastric tube including the steps of:

inserting a gastric tube into the patient's stomach, the gastric tube including a primary suction lumen and a secondary vent lumen each extending to the distal end thereof and being in fluid flow connection at the distal end thereof through a small orifice, the gastric tube forming side holes therethrough in fluid flow communication with the primary lumen and further including an antireflux valve in fluid flow connection with the secondary vent lumen, the gastric tube also including adaptor means for allowing injection of fluid through the antireflux valve into the secondary vent lumen, applying suction through the primary suction lumen while allowing atmospheric air to pass through the adaptor means and antireflux valve into the secondary vent lumen and through the small orifice into the primary lumen, attaching means for injecting fluid to the adaptor means, and injecting the fluid through the antireflux valve into the secondary vent lumen.

* * * * *